United States Patent [19]

Carradine

[11] 4,236,265
[45] Dec. 2, 1980

[54] PORTABLE TRACTION APPARATUS

[76] Inventor: James Carradine, 2331 A, 17th Ave., San Francisco, Calif. 94116

[21] Appl. No.: 18,997

[22] Filed: Mar. 9, 1979

[51] Int. Cl.³ .......................... A61F 5/04; A61G 7/10
[52] U.S. Cl. ............................................. 5/508; 5/84; 5/443; 128/84 R
[58] Field of Search ................. 5/83, 84, 85, 443, 508; 128/84 R, 84 C, 75

[56] References Cited

U.S. PATENT DOCUMENTS

| | | | |
|---|---|---|---|
| 2,259,757 | 10/1941 | Longfellow | 128/84 C |
| 2,370,251 | 2/1945 | Lewis | 5/443 |
| 3,850,165 | 11/1974 | Throner | 5/84 |
| 3,871,366 | 3/1975 | Cotrel | 128/84 C |

Primary Examiner—Casmir A. Nunberg
Attorney, Agent, or Firm—Alfons Puishes

[57] ABSTRACT

A portable bed, cot or "gurney" is modified to produce an apparatus which permits movement of a patient while under full traction. This is accomplished by a novel arrangement of stanchions, longitudinal and cross-bars supporting pulley rope and spring arrangements which form a part of the bed to maintain the traction while the patient is being moved over considerable distances, such as in evacuation operations and similar applications.

3 Claims, 3 Drawing Figures

PORTABLE TRACTION APPARATUS

BACKGROUND OF THE INVENTION

The use of traction upon the body of patients undergoing orthopedic therapy is frequently resorted to. This in essence consists of placing the body in tension and is applied to the neck, shoulders, legs and spinal column in general. For this purpose the relevant parts of the body, such as those mentioned above, are engaged by straps, clamps, belts and various fasteners which in turn are engaged by ropes passing over pulleys from which weights are suspended. In many cases, especially where severe back or neck injuries are involved, this entails the use of a rather extensive combination of ropes, pulleys and counter-weights. These of necessity are customarily supported from the wall or ceiling of the room in which the bed holding the patient is located. Thus when it becomes necessary to move the patient to another location for treatment, x-rays, etc., it is necessary to disconnect the apparatus, thus removing the the traction which may be of serious detriment to the patient. The problem is especially acute when it becomes necessary to evacuate a patient under traction by means of ambulances, aeroplanes or other transportation means.

Numerous different traction devices attached to hospital beds have been constructed and used over a period of years. These are constructed to effect different purposes and in different manners as set forth in more detail below.

U.S. Pat. No. 1,374,115 to Roemer discloses a portable table which is equipped with a crank operated tension device attached to the foot of the patient which, to a considerably limited extent, is applied to put the body in traction to a certain extent and is merely, as its name indicates, a "tension table".

U.S. Pat. No. 2,861,565 to Lapierre describes a selective intermittent or continuous traction device which teaches a novel method of operating traction mechanisms but is not constructed particularly with a view towards portability.

U.S. Pat. No. 2,950,715 to Brobeck for an orthopedic bed teaches a combined traction and exercising device and while it does have portable features, the traction features are rather limited.

U.S. Pat. No. 3,643,996 to Carnahan teaches a wheel chair upon which is superimposed a frame holding a device for placing only a neck in traction.

U.S. Pat. No. 3,699,953 to Mason teaches a novel arrangement of a traction mechanism attached to a bed which permits the patient to operate the traction himself and is adapted to a variety of different types of traction successively. It is not a complete or sophisticated system and not portable.

U.S. Pat. No. 3,800,787 to Rush teaches a traction device attached to a bed especially adapted for applying traction to the lumbar region of the spine by acting on the thighs and femur portions of the patient's legs, while supporting the calves in a horizontal position at a ninety degree angle. It is also not a complete traction system.

U.S. Pat. No. 2,370,251 to Lewis comes the closest to the invention of applicant in application in that it is constructed to be applied to an existing hospital bed. It is described as an "orthopedic arch" which is attached to a bedstead and arranged to hold pulleys and ropes for placing a body in tension. It provides a limited degree of portability but is far from being as sophisticated a device as the invention of applicant's. The provisions for portability with this device are secondary to the construction which permits the attachment and detachment of the device to the bedstead. Many traction elements are lacking.

SUMMARY OF THE INVENTION

Applicant has invented a structure, or apparatus, which may be applied to a portable hospital bed or cot, sometimes referred to as a "gurney" wherein complete and total traction may be effected on the patient while lying on the portable bed and thus permits movement of the patient over considerable distances without releasing the traction. It permits wide range of adjustability of the device, allowing movement of a patient while in traction by ambulances, aeroplanes or other means. It is expecially advantageous in evacuation situations where portability is of paramount importance while maintaining traction on the patient.

The structure is superimposed upon an existing portable bed frame and is characterized by vertical stanchions which are adjustable in height as well as horizontal frame members, both longitudinal and cross, which are adjustable in length and position. A system of ropes and pulleys is supported from this framework and is applied to the patient through neck, waist and leg engaging elements. The adjustable height of the traction frame above the bed frame permits movement of the entire assembly in and through spaces where head room is limited while maintaining the traction elements in effect. Spring mountings for the pulleys aid the portability.

DESCRIPTION OF A PREFERRED EMBODIMENT

Figure 1:
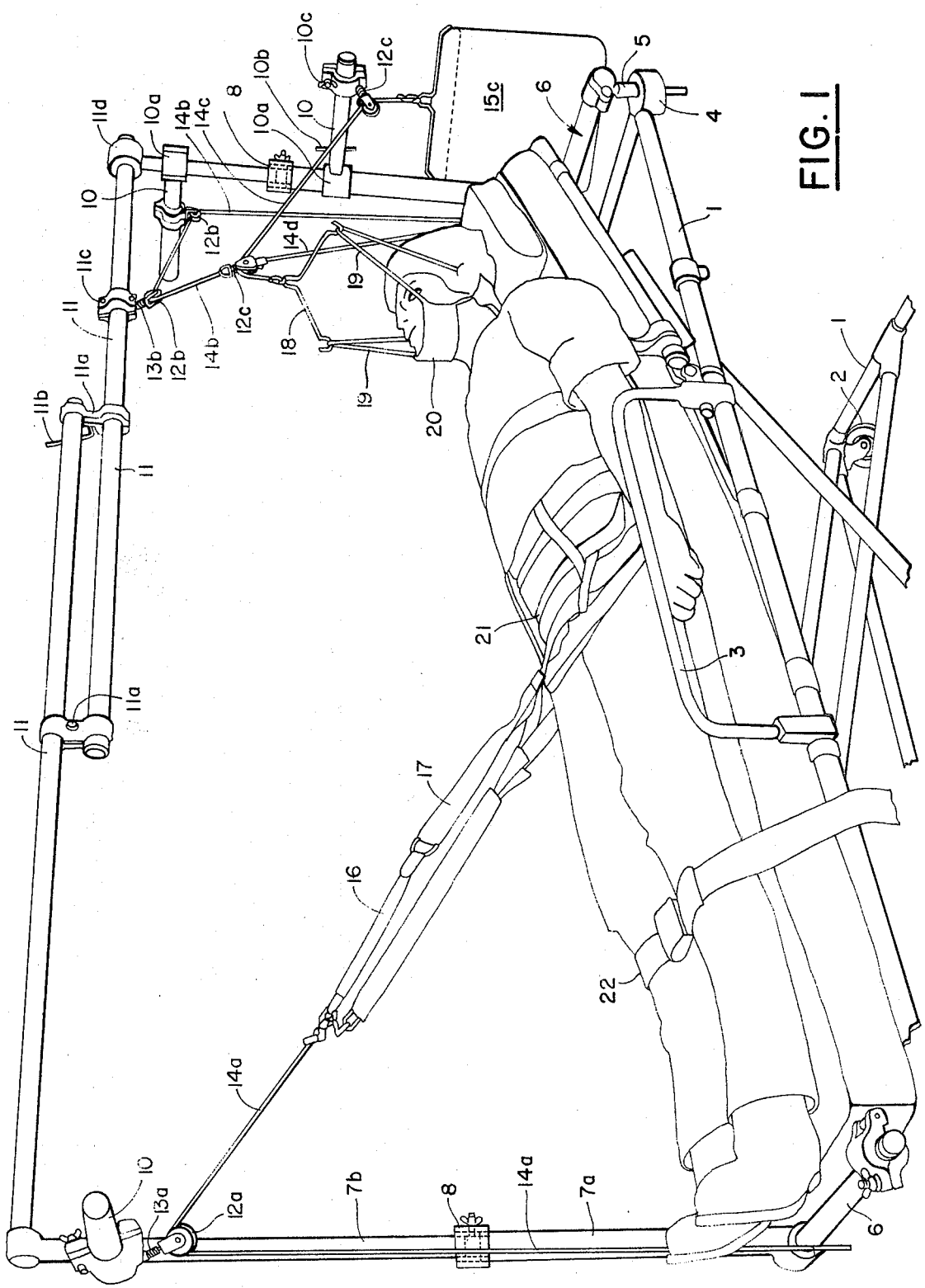
FIG. 1 is a perspective of a patient lying in traction by the use of this invention viewed from the feet end.

Referring now to the figures, there is seen first the members 1 of an existing portable hospital bed, cot or "gurney" frame mounted on wheels or casters 2. The frame 1 is equipped with handlebars 3. Support corner bosses 4 are welded to the corners of frame 1 and are disposed to hold in position short vertical extension members 5. These are disposed to hold in fixed position cross-frame members 6 which act as the horizontal supports for the adjustable superstructure of the apparatus.

Figure 3:
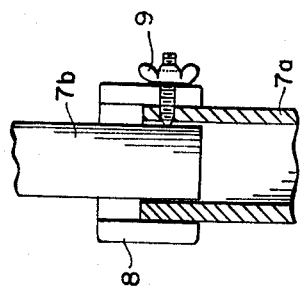
FIG. 3 is a detail showing the adjustable vertical stanchion arrangement.

Vertical stanchions 7 are fixedly positioned on support frame members 6 and are of telescoping construction comprising members 7a and 7b which are held in position by collar 8 and wing nut 9 best seen in detail on FIG. 3.

Upper three transverse members 10 are slidably positioned on stanchions 7 and held at any given position by means of clamps 10a and wing nuts 10b. Positioned also on transverse members 10 are clamp and wing nut combinations 10c which are disposed to hold the rope and pulley members of the apparatus described more fully below.

Positioned on the upper end of stanchions 7 are longitudinal members 11 which are comprised of two parts arranged for lengthwise adjustment by means of double clamps 11a and wing nuts 11b. Longitudinal members 11 are secured to vertical stanchions 7 by means of clamp and wing nut combinations 11d positioned at the ends of longitudinal member 11. Positioned also on longitudinal member 11 is clamp and wing nut combination 11c disposed also to support the rope and pulley arrangement described below.

Figure 2:
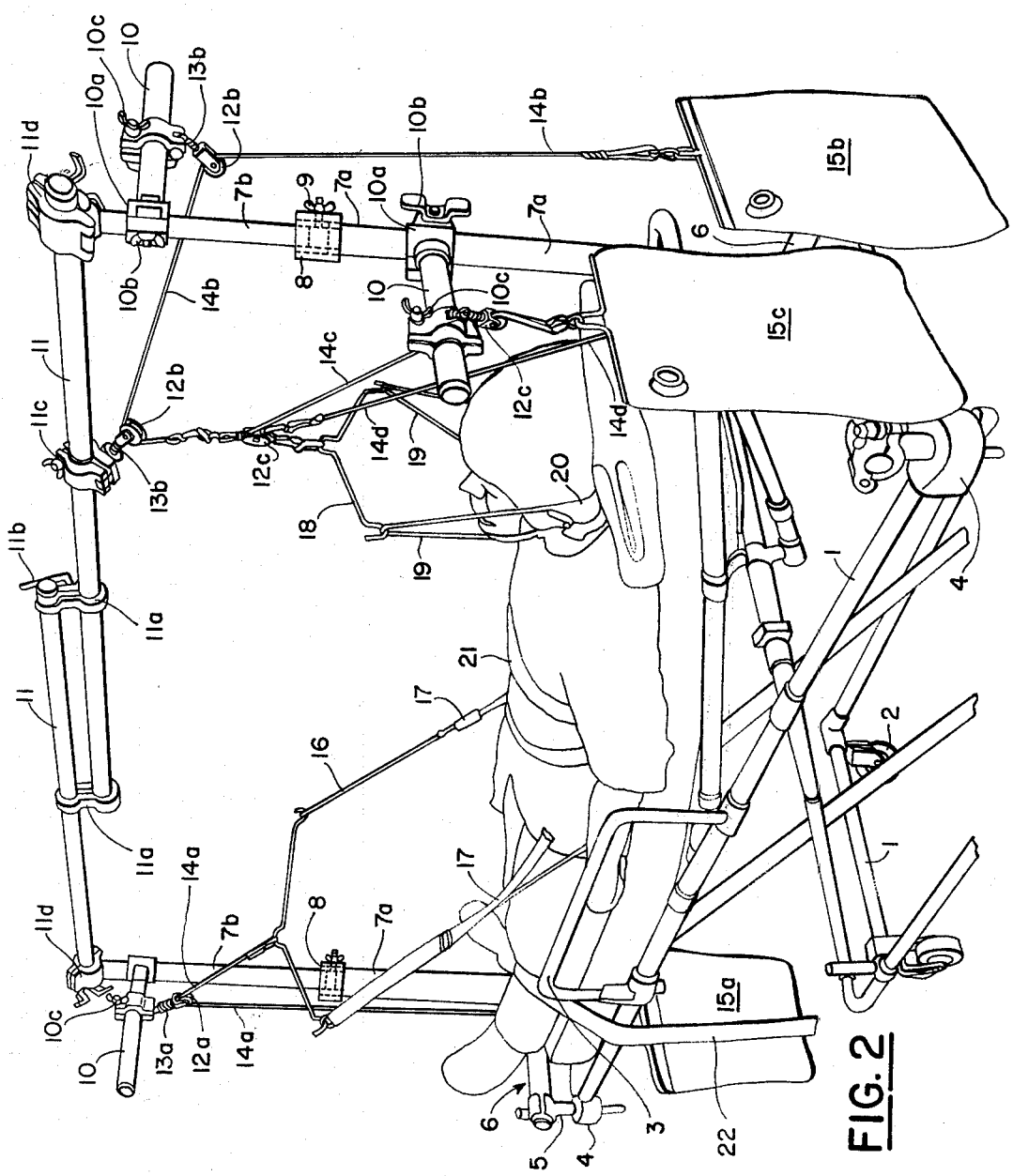
FIG. 2 is a perspective of a patient in traction utilizing this invention viewed from the head end.

Reference should now be had to the foot end of the apparatus as shown in FIGS. 1 and 2. Pulley 12a is suspended from clamp 10c through spring element 13a. Rope 14a is connected to weight 15a at one end and the other end joins metallic yoke 16. Both ends of metallic yoke 16 make connection with straps 17 which are joined to waistband 21 which fits around the waist of the patient. This combination puts the lower portion of the patient's body in tension. It may be modified to engage patient's legs if desired.

Referring now to the head end of the apparatus, the two pulleys 12b are mounted on the longitudinal member 11 and transverse member 10 by means of clamps 11c and 10c respectively through springs 13b. One end of rope 14b which passes over the pulleys 12b is connected to weight 15b and the other end to a suitable loop is fastened to the frame of pulley 12c. Rope 14d secures the frame of pulley 12c to the bed frame, after suitable tension is applied to it through rope 14b and weight 15b. Rope 14c runs over the two pulleys 12c and one end of it is attached to weight 15c. The other end of rope 14c is connected to metal yoke 18 which in turn supports ropes 19 which form a part of the neck traction strap, band, or halter 20 which engages the neck of the patient as shown. Leg straps 22 are shown and may be employed to hold patient's legs down if needed.

It is thus seen that the entire traction apparatus is supported upon and in fact becomes a part of the bed frame when the latter is transported from one location to another. By pushing it on its wheels 2 the entire apparatus moves the patient while maintaining him in the full traction supplied by the action of the members of the apparatus as set forth above.

I claim:

1. A traction apparatus mounted upon and forming a part of a movable bed frame supported on wheels and having a head end and a foot end oppositely spaced thereon comprising:

horizontal cross-frame support members fixedly positioned on said head end and said foot end;

a vertical stanchion fixedly positioned upon each of said frame support members;

a first transverse member slidably mounted upon the stanchion at the foot end of said bed;

a second transverse member slidably mounted on the stanchion at the head end of said bed;

a third transverse member slidably mounted on the stanchion at the head end of said bed above said second transverse member;

a longitudinal member mounted across said stanchion at the top thereof;

a first pulley mounted on said first transverse member;

spring means positioned between said first pulley and said first transverse member;

a first rope engaging said first pulley;

a weight suspended from a first end of said first rope;

means for engaging the waist of a person fastened to the second end of said first rope;

a second pulley mounted on said longitudinal member adjacent said head end of said bed;

spring means positioned between said second pulley and said longitudinal member;

a third pulley mounted on said third transverse member;

spring means positioned between said third pulley and said third transverse member;

a second rope engaging said second and third pulleys;

a weight suspended from the first end of said second rope;

a fourth pulley suspended from the other end of said second rope;

a fifth pulley mounted on said second transverse member;

a third rope engaging said fourth and said fifth pulleys;

a weight suspended from the first end of said third rope;

means for engaging the head and neck of a person fastened to the other end of said third rope;

whereby the body of said person may be maintained in traction while said bed is moved.

2. The apparatus of claim 1 in which said vertical stanchions include means for adjusting their height.

3. The apparatus of claim 1 including means for adjusting the length of said longitudinal member.

* * * * *